United States Patent
Komatsu et al.

(10) Patent No.: US 10,391,283 B2
(45) Date of Patent: Aug. 27, 2019

(54) BALLOON CATHETER AND STENT DELIVERY SYSTEM

(71) Applicant: TERUMO KABUSHIKI KAISHA, Shibuya-ku (JP)

(72) Inventors: Tomoya Komatsu, Hadano (JP); Noboru Saito, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 359 days.

(21) Appl. No.: 14/486,425

(22) Filed: Sep. 15, 2014

(65) Prior Publication Data
US 2015/0005866 A1 Jan. 1, 2015

Related U.S. Application Data

(63) Continuation of application No. PCT/JP2012/084157, filed on Dec. 28, 2012.

(30) Foreign Application Priority Data

Mar. 15, 2012 (JP) .................. 2012-059418

(51) Int. Cl.
*A61M 25/10* (2013.01)
*A61F 2/958* (2013.01)
*A61M 25/00* (2006.01)

(52) U.S. Cl.
CPC ......... *A61M 25/1002* (2013.01); *A61F 2/958* (2013.01); *A61M 25/0021* (2013.01);
(Continued)

(58) Field of Classification Search
CPC .......... A61M 25/1002; A61M 25/0021; A61M 25/0023; A61M 2025/1004; A61M 25/10;
(Continued)

(56) References Cited

U.S. PATENT DOCUMENTS 5,792,172 A * 8/1998 Fischell .................. A61F 2/958
606/194
5,836,965 A * 11/1998 Jendersee ............... A61F 2/958
623/1.11
(Continued)

FOREIGN PATENT DOCUMENTS

| JP | 2003-062080 A | 3/2003 |
| JP | 2008-506454 A | 3/2008 |
| JP | 2010-506655 A | 3/2010 |

OTHER PUBLICATIONS

Notice of Reasons for Rejection dated Jul. 19, 2016 by the Japanese Patent Office in corresponding Japanese Patent Application No. 2014-504644, and an English translation thereof (4 pages).
(Continued)

*Primary Examiner* — Ryan J. Severson
*Assistant Examiner* — Christian D Knauss
(74) *Attorney, Agent, or Firm* — Buchanan Ingersoll & Rooney PC

(57) ABSTRACT

A balloon catheter and a stent delivery system are disclosed, which includes a shaft portion of which an axially orthogonal cross section of an outer peripheral surface has a polygonal shape, and a balloon which is foldable on the outer peripheral surface of the shaft portion and in which turned-back portions are formed when folded. Portions formed to linearly extend along an axial direction in the turned-back portions are respectively positioned on sides of the polygonal shape. A stent can be arranged on an outer periphery of a balloon in the balloon catheter and expands in response to dilation of the balloon.

16 Claims, 5 Drawing Sheets

(52) U.S. Cl.
CPC ... *A61M 25/0023* (2013.01); *A61F 2230/005* (2013.01); *A61F 2230/0017* (2013.01); *A61F 2230/0023* (2013.01); *A61M 25/104* (2013.01); *A61M 25/1006* (2013.01); *A61M 2025/1004* (2013.01)

(58) Field of Classification Search
CPC ............... A61M 25/104; A61F 2/958; A61F 2230/0017; A61F 2230/0019; A61F 2230/0021; A61F 2230/0023; A61F 2230/0026; A61F 2230/005; A61F 2/95
See application file for complete search history.

(56) References Cited

U.S. PATENT DOCUMENTS

| | | | | |
|---|---|---|---|---|
| 6,544,218 B1* | 4/2003 | Choi | .............. | A61B 17/320783 604/96.01 |
| 2001/0037140 A1* | 11/2001 | Gaudoin | ................. | A61F 2/958 623/1.11 |
| 2005/0049609 A1* | 3/2005 | Gunderson | ............. | A61F 2/966 606/108 |
| 2005/0216047 A1* | 9/2005 | Kumoyama | ...... | A61M 25/1027 606/191 |
| 2006/0015134 A1 | 1/2006 | Trinidad | | |
| 2007/0005092 A1* | 1/2007 | Godin | ............... | A61M 25/0023 606/194 |
| 2007/0112407 A1* | 5/2007 | Mertens | .................. | A61F 2/954 623/1.11 |
| 2007/0129748 A1* | 6/2007 | Eidenschink | ........... | A61F 2/958 606/192 |
| 2008/0171977 A1 | 7/2008 | Blix | | |

OTHER PUBLICATIONS

International Search Report (PCT/ISA/210) dated Feb. 19, 2013, by the Japanese Patent Office as the International Searching Authority for International Application No. PCT/JP2012/084157.

* cited by examiner

BALLOON CATHETER AND STENT DELIVERY SYSTEM

CROSS-REFERENCES TO RELATED APPLICATIONS

This application is a continuation of International Application No. PCT/JP2012/084157 filed on Dec. 28, 2012, and claims priority to Japanese Application No. 2012-059418 filed on Mar. 15, 2012, the entire content of both of which is incorporated herein by reference.

TECHNICAL FIELD

The present disclosure relates to a balloon catheter and a stent delivery system for treating a stenosed part occurring inside a living body lumen such as a blood vessel.

BACKGROUND DISCUSSION

Recently, for the medical treatment of myocardial infarction and angina pectoris, for example, a method in which a lesion (stenosed part) of the coronary artery is widened by using a balloon catheter is performed. A similar method can be performed for treating a stenosed part formed inside another blood vessel, the bile duct, the trachea, the esophagus, the urethra and other living body lumens as well.

The balloon catheter generally includes an elongated shaft portion and a balloon, which is provided, on a distal end side of the shaft portion while being dilatable in a radial direction. After a contracted balloon reaches a target part in the body via the inside of a thin living body lumen, the stenosed part can be widened by dilating the balloon.

Accordingly, the balloon needs to be thinly contracted until the balloon reaches the target part. JP-A-2003-62080 discloses a method in which the balloon is folded so as to be wound around an outer peripheral surface of the shaft portion in a circumferential direction.

When a balloon is wound around an outer peripheral surface of the shaft portion while being folded, a turned-back portion can be formed in the balloon causing an outer diameter of an axially perpendicular cross section to be enlarged due to a bulge of the turned-back portion of the balloon, and thus, it may be difficult to be inserted into a thin living body lumen. In a case where the outer diameter of the shaft portion is reduced to be able to obtain an expected outer diameter of the axially perpendicular cross section when the balloon is folded, flexural rigidity of the shaft portion is degraded, resulting in degradation of deliverability of a catheter. Regarding a stent delivery system in which a stent is arranged on an outer periphery of the balloon, which is similar to the balloon catheter, concerns that it may be difficult to be inserted into the thin living body lumen or degradation of the deliverability of a catheter can occur.

The present disclosure provides a balloon catheter and a stent delivery system in which high deliverability can be maintained without degrading flexural rigidity of the shaft portion, and can reduce the outer diameter at the time the balloon is folded.

SUMMARY

In accordance with an exemplary embodiment, a balloon catheter is disclosed, which includes a shaft portion of which an axially orthogonal cross section of an outer peripheral surface has a polygonal shape, and a balloon which is foldable on the outer peripheral surface of the shaft portion and in which turned-back portions are formed when folded. Portions formed to linearly extend along an axial direction in the turned-back portions are respectively positioned on sides of the polygonal shape.

In accordance with an exemplary embodiment, a stent delivery system is disclosed, which includes the balloon catheter, and a stent that is arranged on an outer periphery of a balloon in the balloon catheter and expands in response to dilation of the balloon.

In a balloon catheter and a stent delivery system having the above-disclosed configurations, portions formed to linearly extend along an axial direction in turned-back portions of a balloon are respectively positioned on sides of a polygonal shape on an outer peripheral surface of a shaft portion. Therefore, high flexural rigidity can be maintained on account of presence of corner portions in the polygonal shape, and an outer diameter at the time the balloon is folded can be reduced by suppressing the turned-back portions from protruding in a radial direction, and thus, relatively high deliverability can be maintained and a reduction in diameter of the balloon catheter and the stent delivery system can be achieved.

In accordance with an exemplary embodiment, when an axially orthogonal cross section of the outer peripheral surface has a regular polygonal shape, relief amounts on each of the sides with respect to the corner portions become uniform, and thus, a reduction in diameter can be efficiently achieved, and high operability by suppressing anisotropy in the flexural rigidity can be maintained.

In accordance with an exemplary embodiment, when the portions formed to linearly extend along the axial direction in the turned-back portions are provided to be a multiple of the number of corners in the polygonal shape and are respectively positioned on the sides of the polygonal shape to be equal in number, the portions are equally arranged on each of the sides, and thus, the reduction in diameter can be effectively achieved.

In accordance with an exemplary embodiment, when the axially orthogonal cross section of an inner peripheral surface of the shaft portion has a polygonal shape with corners having the same number as that of the outer peripheral surface, high flexural rigidity of the shaft portion can be maintained and a wide internal space can be secured.

In accordance with an exemplary embodiment, when portions corresponding to the sides of the polygonal shape on the outer peripheral surface are formed to be recessed, a bulge of the turned-back portion can be efficiently accommodated and the reduction in diameter can be more efficiently achieved.

In accordance with an exemplary embodiment, when the number of corners in the polygonal shape on the outer peripheral surface ranges from three to ten, the relief amount for accommodating the turned-back portion can be sufficiently secured without causing the outer diameter of the shaft portion to be excessively large.

In accordance with an exemplary embodiment, a balloon catheter is disclosed comprising: a shaft portion of which an axially orthogonal cross section of an outer peripheral surface has a polygonal shape, wherein each angle of the polygonal shape is equal in measure and each side of the polygonal shape has a same length; a balloon which is foldable on the outer peripheral surface of the shaft portion and in which turned-back portions are formed when folded; and wherein portions formed to linearly extend along an axial direction in the turned-back portions are respectively positioned on sides of the polygonal shape.

In accordance with an exemplary embodiment, a method is disclosed of folding a balloon around a balloon shaft portion of a balloon catheter, the balloon shaft portion of which an axially orthogonal cross section of an outer peripheral surface has a polygonal shape, comprising: forming turned-back portions when folding the balloon on the outer peripheral surface of the balloon shaft portion; and positioning portions formed to linearly extend along an axial direction in the turned-back portions on sides of the polygonal shape

DETAILED DESCRIPTION

Figure 1:
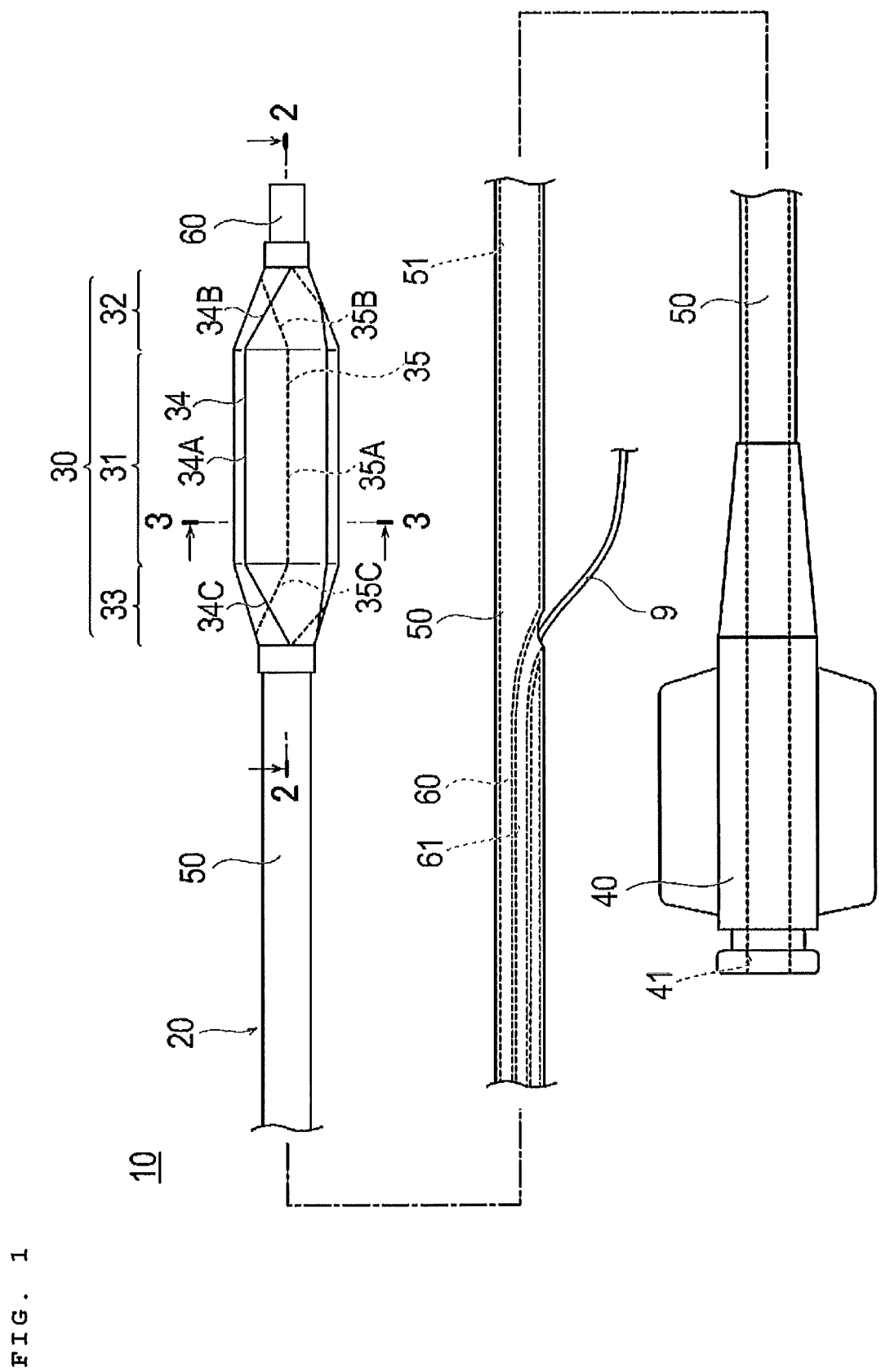
FIG. 1 is a side view of an exemplary balloon catheter according to an exemplary embodiment of the present disclosure.

Hereinafter, an embodiment of the present disclosure will be described with reference to the drawings. There are cases where dimension ratios in the drawings are exaggerated for convenience of descriptions, thereby being different from the actual ratio of the drawings.

A balloon catheter 10 of the present disclosure can be used for treating a stenosed part formed inside a blood vessel, the bile duct, the trachea, the esophagus, the urethra and other living body lumens. In this disclosure, a side to be inserted into a living body lumen is referred to as "distal end" or "distal end side", and an operator side is referred as "proximal end" or "proximal end side".

As illustrated in FIG. 1, the balloon catheter 10 has an elongated catheter main body portion 20, a balloon 30 which is provided in a distal end portion of the catheter main body portion 20, and a hub 40 which is fixedly attached to a proximal end of the catheter main body portion 20.

The catheter main body portion 20 is provided with an outer tube 50 which is a tubular body having an open distal end and proximal end, and an inner tube 60 (shaft portion) which is arranged inside the outer tube 50. Inside the outer tube 50, a dilation lumen 51 in which a dilation fluid for dilating the balloon 30 flows can be formed. Inside the inner tube 60, a guide wire lumen 61 through which a guide wire 9 is inserted is formed. The dilation fluid may be a gas as well as a liquid. For example, gases such as helium gas, $CO_2$ gas and $O_2$ gas, and liquids such as a physiological saline solution and a contrast medium can be exemplified.

Figure 2:
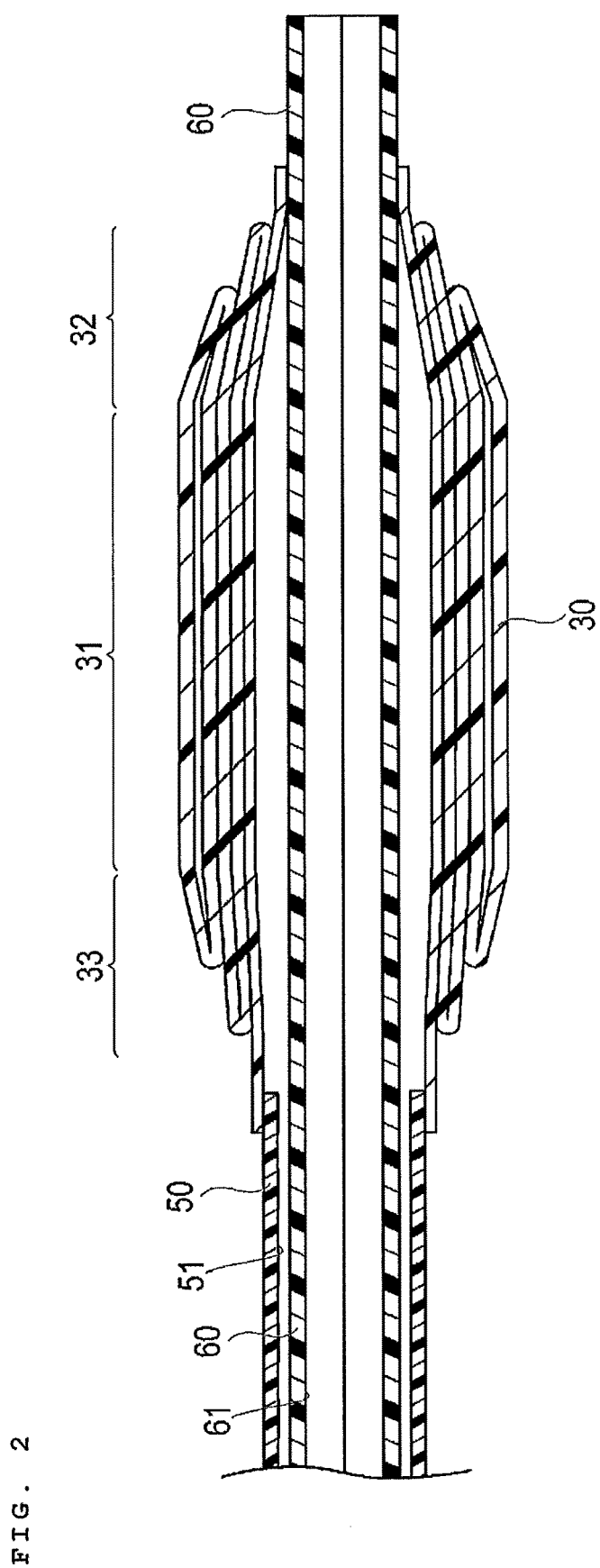
FIG. 2 is a longitudinal sectional view of a distal end portion of the balloon catheter taken along line 2-2 in FIG. 1.
Figure 3:
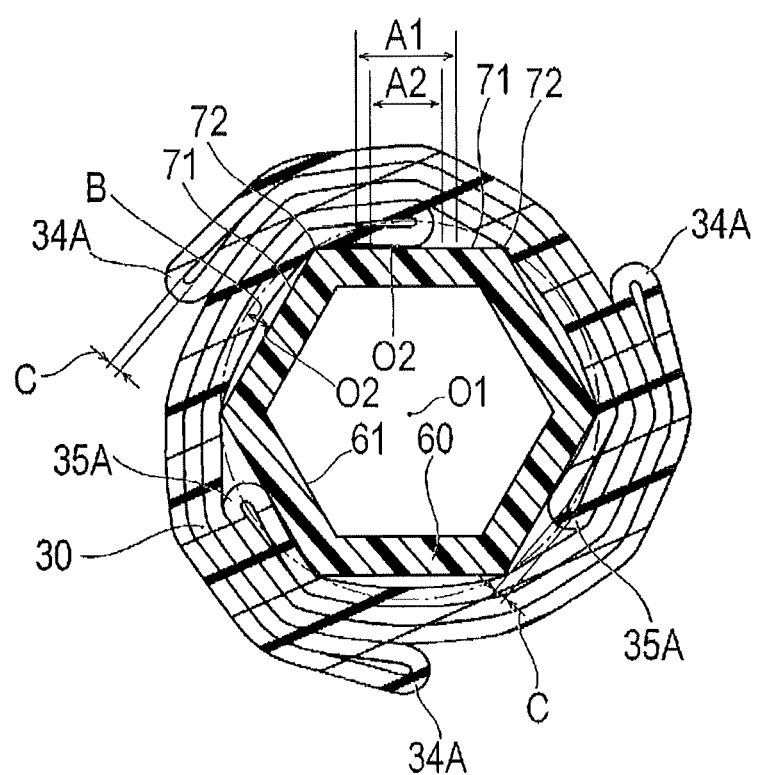
FIG. 3 is a lateral sectional view of the balloon catheter taken along line 3-3 in FIG. 1.

As illustrated in FIG. 2, a distal end portion of the inner tube 60 penetrates the inside of the balloon 30 and is open on the further distal end side than the balloon 30. As illustrated in FIG. 1, a proximal end side of the inner tube 60 penetrates a side wall of the outer tube 50, thereby being fixedly attached to the outer tube 50 in a liquid-tight manner by an adhesive or heat fusion. As illustrated in FIG. 3, in the inner tube 60, a cross section which is orthogonal to an axis of an outer peripheral surface (hereinafter, refer to as axially orthogonal cross section) has a regular hexagonal shape and corner portions 72 and sides 71 are included. In the inner tube 60, the axially orthogonal cross section of an inner peripheral surface has the regular hexagonal shape, which can be concentric with the axially orthogonal cross section of the outer peripheral surface and includes corner portions in the same direction. Therefore, the thicknesses of portions corresponding to the sides 71 of the inner tube 60 are uniform on all six sides. A distance between a middle portion O2 of the side 71 on the outer peripheral surface of the inner tube 60 and a center portion O1 of the inner tube 60 can be shorter than a distance between the corner portion 72 of the hexagonal shape of the outer peripheral surface of the inner tube 60 and the center portion O1 of the inner tube 60 by a relief amount B.

As illustrated in FIG. 1, the hub 40 includes a proximal end opening portion 41 functioning as a port which communicates with the dilation lumen 51 of the outer tube 50 and allows the dilation fluid to flow in and out. The proximal end portion of the outer tube 50 can be fixedly attached to the hub 40 in a liquid-tight manner by an adhesive, heat fusion, a fastener (not illustrated) or the like.

For example, it can be preferable that the outer tube 50 and the inner tube 60 are formed with a material having certain flexibility. For example, such materials can include polyolefin such as polyethylene, polypropylene, polybutene, an ethylene-propylene copolymer, an ethylene-vinyl acetate copolymer, an ionomer and a mixture of two or more thereof, a soft polyvinyl chloride resin, polyamide, a polyamide elastomer, polyester, a polyester elastomer, polyurethane, a thermoplastic resin such as a fluorocarbon resin, silicone rubber and latex rubber.

As examples for a constituting material of the hub 40, a thermoplastic resin such as polycarbonate, polyamide, polysulfone, polyarylate and a methacrylate butylene styrene copolymer can be suitably used.

Figure 4:
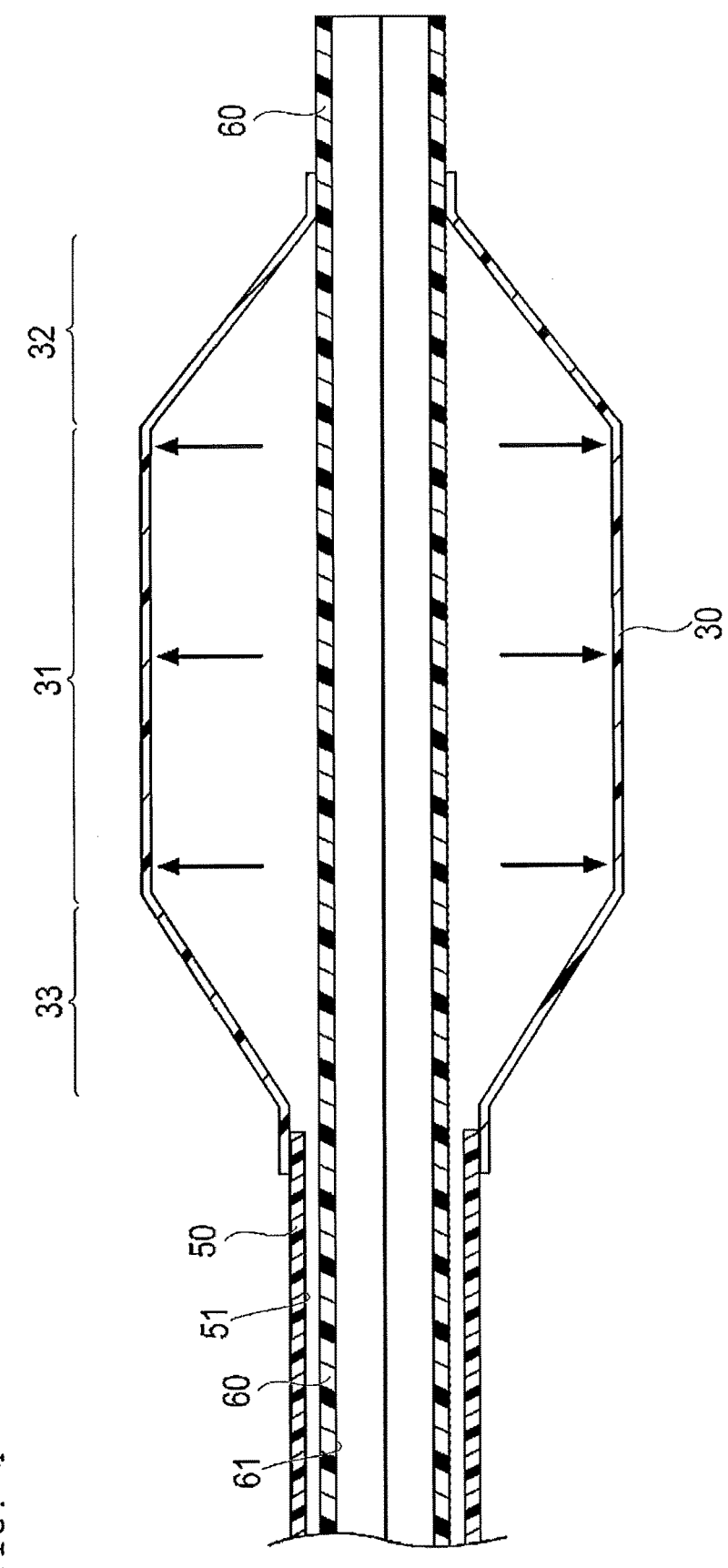
FIG. 4 is a longitudinal sectional view illustrating a balloon of the balloon catheter when dilated.

The balloon 30 widens a stenosed part through dilation. In a case of a stent delivery system in which a stent can be arranged on an outer periphery of the balloon 30, the balloon 30 causes the stent to expand. As in FIG. 4 illustrating a state where the balloon 30 is dilated, the balloon 30 is formed to be substantially cylindrical at a middle portion in an axial direction and includes a tubular portion 31 having an approximately uniform diameter to be able to efficiently dilate in a predetermined range. The axially orthogonal cross section of the tubular portion 31 does not necessarily have a circular shape. On a distal end side of the tubular portion 31 of the balloon 30, a first decreased diameter portion 32 can be provided in which the diameter is formed to decrease in a tapered state toward the distal end side. On a proximal end side of the tubular portion 31, a second decreased diameter portion 33 can be provided in which the diameter is formed to decrease in the tapered state toward the proximal end side.

In accordance with an exemplary embodiment, the distal end side of the first decreased diameter portion 32 can be fixedly attached to an outer wall surface of the inner tube 60 in a liquid-tight manner by an adhesive, heat fusion and the like. The proximal end side of the second decreased diameter portion 33 can be fixedly attached to an outer wall surface of the distal end portion of the outer tube 50 in a liquid-tight manner by an adhesive, heat fusion and the like. Therefore, the inside of the balloon 30 communicates with the dilation lumen 51 which can be formed in the outer tube 50 to allow the dilation fluid to flow in from the proximal end side via the dilation lumen 51. The balloon 30 dilates due to the inflow of the dilation fluid, and comes into a folded state by discharging the dilation fluid, which has flowed in.

As illustrated in FIGS. 1 to 3, when in a non-dilation state, the balloon 30 can be shaped to be wound around the outer peripheral surface of the inner tube 60 in a circumferential direction and to be in the folded state. The above-described balloon 30 can be molded through blow molding in which in a die, a tube (material) is heated, is pressurized so as to be bulged by a fluid from the inside, and is pressed against a die.

The balloon 30 can be folded so as to be wound around the inner tube 60, thereby forming turned-back portions 34 and 35. The turned-back portions 34 and 35 respectively include three outer turned-back portions 34 which are turned back to be convex in a radially outer direction and three inner turned-back portions 35 which are turned back to be convex in a radially inner direction. In the present embodiment, the outer turned-back portions 34 and the inner turned-back portions 35 can be arranged to be alternately disposed in the circumferential direction so as not to overlap with each other when in the folded state. As the outer turned-back portions 34 and the inner turned-back portions 35 are turned back, a gap C (refer to FIG. 3) is formed in the outer turned-back portion 34 and the inner turned-back portion 35, thereby having a bulge as much as a thickness of the gap C in a thickness direction.

The outer turned-back portion 34 includes a first outer turned-back portion 34A which is formed to linearly extend along the axial direction within a range corresponding to the tubular portion 31, that is, in the middle portion of the balloon 30 in the axial direction. The outer turned-back portion 34 also includes a second outer turned-back portion 34B on a distal end side (range corresponding to first decreased diameter portion 32) of the first outer turned-back portion 34A and includes a third outer turned-back portion 34C on a proximal end side (range corresponding to second decreased diameter portion 33) of the first outer turned-back portion 34A. The inner turned-back portion 35 includes a first inner turned-back portion 35A which is formed to linearly extend along the axial direction within a range corresponding to the tubular portion 31, that is, in the middle portion of the balloon 30 in the axial direction. The inner turned-back portion 35 also includes a second inner turned-back portion 35B on a distal end side (range corresponding to first decreased diameter portion 32) of the first inner turned-back portion 35A and includes a third inner turned-back portion 35C on a proximal end side (range corresponding to second decreased diameter portion 33) of the first inner turned-back portion 35A.

Each of the first outer turned-back portions 34A and each of the first inner turned-back portions 35A are arranged on each of six sides 71 of the hexagonal cross section of the inner tube 60 one by one without overlapping each other. As each of the first outer turned-back portions 34A and each of the first inner turned-back portions 35A are arranged on each of the six sides 71 of the hexagonal cross section of the inner tube 60 one by one, all the bulges caused by the gaps C of the first outer turned-back portions 34A and the first inner turned-back portions 35A are respectively accommodated in each of sides 71 of which the distance from the center portion O1 of the inner tube 60 is shorter than that from the corner portion 72 as much as the relief amount B. For example, it can be preferable that the thicknesses of the gaps C of the first outer turned-back portions 34A and the first inner turned-back portions 35A are equal to or less than the relief amount B so as not to cause the first outer turned-back portions 34A and the first inner turned-back portions 35A to protrude in a radial direction. However, the thicknesses of the gaps C are not necessarily to be equal to or less than the relief amount B.

As disclosed above, since the axially orthogonal cross section of the outer peripheral surface of the inner tube 60 has the polygonal shape, high flexural rigidity is maintained on account of the corner portions 72, and the first outer turned-back portions 34A and the first inner turned-back portions 35A can be suppressed from protruding in the radial direction utilizing the relief amounts B, thereby reducing an outer diameter of the balloon catheter at the time the balloon 30 is folded. Thus, relatively high deliverability of the balloon catheter can be maintained while achieving a reduction in diameter of the balloon 30

In accordance with an exemplary embodiment, it can be preferable that all the first outer turned-back portions 34A and the first inner turned-back portions 35A are positioned within a range of plus/minus one-fourth from the middle portion O2 of each side 71 in the length of the side 71, that is, within a range of half the side 71 in the middle (refer to A1 in FIG. 3). For example, it can be more preferable to be positioned within a range of plus/minus one-sixth from the middle portion O2 of each side 71 in the length of the side 71, that is, within a range of one-third the side 71 in the middle (refer to A2 in FIG. 3), and it is further preferable to accord with the middle portion O2 on each side 71. As the first outer turned-back portions 34A and the first inner turned-back portions 35A are positioned on the middle portion O2 on each side 71 or in the vicinity thereof, the first outer turned-back portions 34A and the first inner turned-back portions 35A can be more effectively suppressed from protruding in the radial direction.

It can be preferable that the balloon 30 be formed of a material having certain flexibility. For example, such materials can include polyolefin such as polyethylene, polypropylene, polybutene, an ethylene-propylene copolymer, an ethylene-vinyl acetate copolymer, an ionomer and a mixture of two or more thereof, a soft polyvinyl chloride resin, polyamide, a polyamide elastomer, polyester, a polyester elastomer, polyurethane, a thermoplastic resin such as a fluorocarbon resin, silicone rubber and latex rubber.

Subsequently, an operation of the balloon catheter 10 according to the present disclosure will be described through an example in which the balloon catheter 10 is used being inserted into a blood vessel.

In accordance with an exemplary embodiment, initially, for example, before treating a stenosed part in a blood vessel, the insides of the balloon 30 and the dilation lumen 51 are deflated so that the dilation fluid is replaced inside the balloon 30 and the dilation lumen 51. In this case, the balloon 30 is in the folded state (FIGS. 1 to 3).

Subsequently, a sheath is indwelled in a blood vessel of a patient by Seldinger's method, for example, while the guide wire 9 is in a state of being inserted through the inside of the guide wire lumen 61, thereby inserting the guide wire 9 and the balloon catheter 10 into the blood vessel through the inside of the sheath. Successively, the balloon catheter 10 is moved forward while the guide wire 9 is moved in advance so that the balloon 30 reaches the stenosed part.

Subsequently, in a state where the balloon 30 is positioned in the stenosed part, a predetermined amount of the dilation fluid is injected in the balloon 30 through the proximal end opening portion 41 of the hub 40 using an indeflator, a syringe, a pump and the like. The dilation fluid flows into the balloon 30 through the dilation lumen 51, thereby dilating the folded balloon 30, as illustrated in FIG. 4. Accordingly, the tubular portion 31 of the balloon 30 can widen the stenosed part. In case of being used as the stent delivery system in which the stent is arranged on the outer periphery of the balloon 30, the stent can expand while being plastically deformed, and thus, favorably maintain the state where the stenosed part is widened by the stent.

Thereafter, the dilation fluid is suctioned through the proximal end opening portion 41 to be discharged, and then, the balloon 30 is contracted into the folded state. In the case of being used as the stent delivery system, the stent is indwelled in the stenosed part as the stent is in an expanded state. Thereafter, the guide wire 9 and the balloon catheter 10 are withdrawn from the blood vessel via the sheath, thereby completing the procedure.

As disclosed above, the balloon catheter 10 of the exemplary embodiment can include an inner tube 60 (shaft portion) of which the axially orthogonal cross section of the outer peripheral surface has the polygonal shape, and the balloon 30 which is foldable on the outer peripheral surface of the inner tube 60 and in which the turned-back portions 34 and 35 are formed when folded. In the balloon catheter 10, portions (first outer turned-back portion 34A and first inner turned-back portion 35A) formed to linearly extend along the axial direction in the turned-back portions 34 and 35 are respectively positioned on sides 71 of the polygonal shape. Therefore, high flexural rigidity is maintained on account of presence of the corner portions 72 in the polygonal shape of the inner tube 60, and the first outer turned-back portions 34A and the first inner turned-back portions 35A are suppressed from protruding in the radial direction utilizing the relief amounts B of the sides 71, thereby reducing the outer diameter at the time the balloon 30 is folded. Thus, relatively high deliverability of the balloon catheter 10 can be maintained while achieving a reduction in diameter of the balloon. The above-described balloon catheter 10 having high flexural rigidity and improved deliverability is particularly effective when treating a part having a little bent inside a lumen, for example, a lesion site of the below knee artery (BK) by trans femoral approach (TFA).

Since the axially orthogonal cross section of the outer peripheral surface of the inner tube 60 has a regular polygonal shape, the relief amounts B on each of the sides 71 are uniform, and thus, the reduction in diameter can be efficiently achieved, and a high operability by suppressing anisotropy in the flexural rigidity can be maintained. In accordance with an exemplary embodiment, for example, as shown in FIG. 3, a regular polygonal shape is a polygonal shape that is equiangular (all angles are equal in measure) and equilateral (all sides have the same length).

Since the first outer turned-back portions 34A and the first inner turned-back portions 35A are provided to be a multiple of the number of corners (same number in the present embodiment) in the polygonal shape and are respectively positioned on the sides 71 of the polygonal shape to be equal in number (one at a time in the present embodiment), the turned-back portions are equally arranged, and thus, the reduction in diameter of the balloon catheter 10 can be effectively achieved.

Since the axially orthogonal cross section of the inner peripheral surface of the inner tube 60 has the polygonal shape with corners having the same number as that of the outer peripheral surface, relatively high flexural rigidity of the inner tube 60 can be maintained and a wide internal space (guide wire lumen 61) can be secured. An area that comes into contact with the guide wire 9 passing through the internal space can be smaller compared to a case of a cross section having a circular shape so that sliding resistance of the guide wire 9 is lowered, thereby improving the operability.

Figure 5:
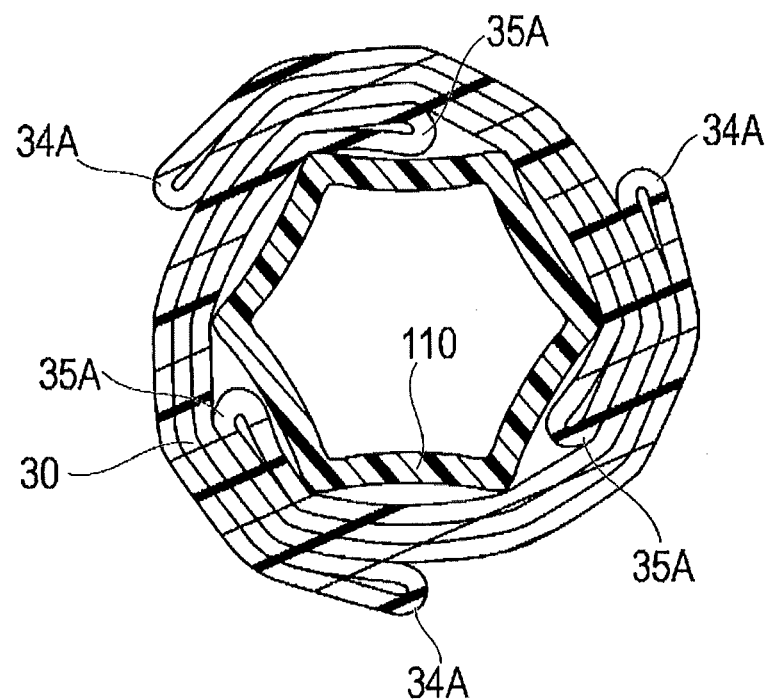
FIG. 5 is a lateral sectional view illustrating an exemplary balloon catheter according to an exemplary embodiment of the present disclosure.

The present disclosure is not limited to only the exemplary embodiments disclosed herein, and thus, various changes can be made by those skilled in the art within the technical ideas of the present disclosure. For example, as in a modification example illustrated in FIG. 5, the shape of the axially orthogonal cross section of the outer peripheral surface and the inner peripheral surface of an inner tube 110 can have a shape in which sides of the polygonal shape are recessed. In such a configuration, the bulges of the first outer turned-back portions 34A and the first inner turned-back portions 35A can be more efficiently accommodated.

In the present disclosure, although the shape of the cross section of the inner tube 60 has the regular polygonal shape, it is not necessary to have the regular polygonal shape.

The axially orthogonal cross section of the inner peripheral surface of the inner tube 60 may not have the polygonal shape and it may have a circular shape, for example.

The number of corners of the axially orthogonal cross section of the outer peripheral surface of the inner tube 60 is not limited to six. When there are fewer corners than are necessary, the outer diameter becomes large due to securing necessary flexural rigidity, and when there are excessive corners more than are necessary, the relief amounts B for the first outer turned-back portions 34A and the first inner turned-back portions 35A become small. Therefore, it can be preferable that the number of corners range from three to ten, and it can be more preferable to range from three to eight. In accordance with an exemplary embodiment, it can be preferable that the number of turned-back portions of the balloon 30 change in accordance with the number of corners of the axially orthogonal cross section of the outer peripheral surface of the inner tube 60.

Figure 6:
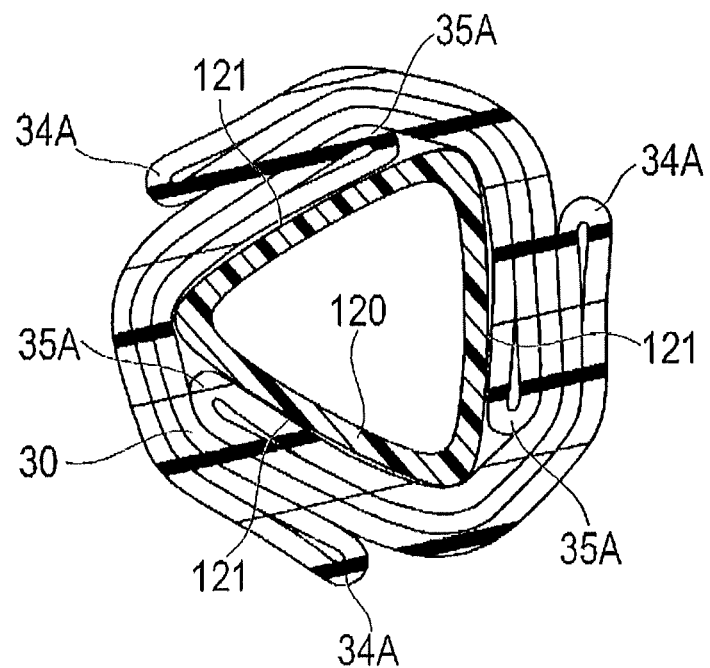
FIG. 6 is a lateral sectional view illustrating an exemplary balloon catheter according to an exemplary embodiment of the present disclosure.

In accordance with an exemplary embodiment, as illustrated in FIG. 6, a plurality of the first outer turned-back portions 34A and the first inner turned-back portions 35A may be provided on one side 121 of an inner tube 120. In this case, it can be preferable that the first outer turned-back portions 34A and the first inner turned-back portions 35A is provided on each of the sides 121 to be equal in number (two in FIG. 6). In this manner, as the first outer turned-back portions 34A and the first inner turned-back portions 35A are equally arranged, the reduction in diameter of the balloon catheter can be effectively achieved. As illustrated in FIG. 6, the polygonal shape may have sides and corners formed to include curved surfaces, or the corner portions of the polygonal shape may be chamfered.

The detailed description above describes a balloon catheter and a stent delivery system. The disclosure is not limited, however, to the precise embodiments and variations described. Various changes, modifications and equivalents can effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A balloon catheter comprising:
   a shaft portion of which an axially orthogonal cross section of an outer peripheral surface has a polygonal shape;
   a balloon which is folded around the outer peripheral surface of the shaft portion and in which turned-back portions are formed, and wherein the turned-back portions include outer turned-back portions which are turned back to be convex in a radially outer direction and inner turned-back portions which are turned back to be convex in a radially inner direction, and wherein at least a portion of the balloon is arranged between a lower portion of the outer turned-back portions and an upper portion of the inner turned-back portions;

wherein portions formed to linearly extend along an axial direction in the turned-back portions are respectively positioned on sides of the polygonal shape;

wherein the outer turned-back portions and the inner turned-back portions are arranged to be alternately disposed in the circumferential direction so as not to overlap with each other when in a folded state, and wherein each of the sides of the polygonal shape has at least one of the outer turned-back portions or the inner turned-back portions; and the turned-back portions being disposed on a side of the outer peripheral surface of the polygonal shape of the shaft portion.

2. The balloon catheter according to claim 1, wherein the turned-back portions contact the side of the outer peripheral surface of the polygonal shape of the shaft portion.

3. The balloon catheter according to claim 2, wherein the inner turned-back portions contact the side of the outer peripheral surface of the polygonal shape of the shaft portion and the outer turned-back portions are disposed above the outer peripheral surface of the polygonal shape of the shaft portion.

4. The balloon catheter according to claim 1, wherein a number of the turned-back portions is the same as a number of the sides of the outer peripheral surface of the polygonal shape of the shaft portion and each of the turned-back portions are disposed on different sides of the outer peripheral surface of the polygonal shape of the shaft portion.

5. The balloon catheter according to claim 1, wherein a number of turned-back portions is the same as a number of sides of the outer peripheral surface of the polygonal shape of the shaft portion and the turned-back portions are disposed on each side of the outer peripheral surface of the polygonal shape of the shaft portion.

6. A balloon catheter comprising:
a shaft portion of which an axially orthogonal cross section of an outer peripheral surface has a polygonal shape, wherein each angle of the polygonal shape is equal in measure and each side of the polygonal shape has a same length;
a balloon which is folded around the outer peripheral surface of the shaft portion and in which turned-back portions are formed, and wherein the turned-back portions include outer turned-back portions which are turned back to be convex in a radially outer direction and inner turned-back portions which are turned back to be convex in a radially inner direction, and wherein at least a portion of the balloon is arranged between a lower portion of the outer turned-back portions and an upper portion of the inner turned-back portions;
wherein portions formed to linearly extend along an axial direction in the turned-back portions are respectively positioned on the sides of the polygonal shape; and
wherein the outer turned-back portions and the inner turned-back portions are arranged to be alternately disposed in the circumferential direction and equidistant from adjacent turned-back portions so as not to overlap with each other when in a folded state, wherein the each side of the polygonal shape has at least one of the outer turned-back portions or the inner turned-back portions.

7. The balloon catheter according to claim 6,
wherein the portions formed to linearly extend along the axial direction in the turned-back portions are provided to be a multiple of a number of corners in the polygonal shape, and are respectively positioned on the sides of the polygonal shape to be equal in number.

8. The balloon catheter according to claim 6,
wherein an axially orthogonal cross section of an inner peripheral surface of the shaft portion has a polygonal shape with corners having a same number as that of the outer peripheral surface.

9. The balloon catheter according to claim 6,
wherein portions corresponding to the sides of the polygonal shape on the outer peripheral surface are recessed.

10. The balloon catheter according to claim 6,
wherein a number of corners in the polygonal shape of the outer peripheral surface ranges from four to ten.

11. A method of folding a balloon around a balloon shaft portion of a balloon catheter, the balloon shaft portion of which an axially orthogonal cross section of an outer peripheral surface has a polygonal shape, comprising:
forming turned-back portions when folding the balloon around the outer peripheral surface of the balloon shaft portion, the turned-back portions including outer turned-back portions which are turned back to be convex in a radially outer direction and inner turned-back portions which are turned back to be convex in a radially inner direction, and wherein at least a portion of the balloon is arranged between a lower portion of the outer turned-back portions and an upper portion of the inner turned-back portions;
positioning portions formed to linearly extend along an axial direction in the turned-back portions on sides of the polygonal shape; and
arranging the outer turned-back portions and the inner turned-back portions to be alternately disposed in the circumferential direction so as not to overlap with each other when in a folded state, and wherein each of the sides of the polygonal shape has at least one of the outer turned-back portions or the inner turned-back portions, and the turned-back portions being disposed on a side of the outer peripheral surface of the polygonal shape of the balloon shaft portion.

12. The method according to claim 11, wherein a number of corners in the polygonal shape of the outer peripheral surface is six, and wherein the turned-back portions include three outer turned-back portions which are turned back to be convex in a radially outer direction and three inner turned-back portions which are turned back to be convex in a radially inner direction, the method comprising:
arranging the three outer turned-back portions and the three inner turned-back portions to be alternately disposed in a circumferential direction so as not to overlap with each other when in a folded state.

13. The method according to claim 11, wherein the turned-back portions contact the side of the outer peripheral surface of the polygonal shape of the balloon shaft portion.

14. The method according to claim 13, wherein the inner turned-back portions contact the side of the outer peripheral surface of the polygonal shape of the balloon shaft portion and the outer turned-back portions are disposed above the outer peripheral surface of the polygonal shape of the balloon shaft portion.

15. The method according to claim 11, wherein a number of the turned-back portions is the same as a number of the sides of the outer peripheral surface of the polygonal shape of the balloon shaft portion and each of the turned-back portions are disposed on different sides of the outer peripheral surface of the polygonal shape of the balloon shaft portion.

16. The method according to claim 11, wherein a number of turned-back portions is the same as a number of sides of the outer peripheral surface of the polygonal shape of the balloon shaft portion and each of the turned-back portions is disposed on each side of the outer peripheral surface of the polygonal shape of the balloon shaft portion.

* * * * *